(12) United States Patent
Maurice

(10) Patent No.: US 10,173,034 B2
(45) Date of Patent: Jan. 8, 2019

(54) CATHETERIZATION DEVICE COMPRISING A CATHETER, WHICH HAS A DEFLECTABLE STEERING END, AND A CONTROL DEVICE FOR CONTROLLING THE CATHETER

(71) Applicant: VascoMed GmbH, Binzen (DE)

(72) Inventor: Ingmar Maurice, Amsterdam (NL)

(73) Assignee: VascoMed GmbH, Binzen (DE)

( * ) Notice: Subject to any disclaimer, the term of this patent is extended or adjusted under 35 U.S.C. 154(b) by 816 days.

(21) Appl. No.: 14/472,591

(22) Filed: Aug. 29, 2014

(65) Prior Publication Data

US 2015/0088061 A1 Mar. 26, 2015

Related U.S. Application Data

(60) Provisional application No. 61/881,977, filed on Sep. 25, 2013.

(51) Int. Cl.
*A61M 25/01* (2006.01)

(52) U.S. Cl.
CPC .... *A61M 25/0133* (2013.01); *A61M 25/0136* (2013.01); *A61M 25/0138* (2013.01); *A61M 25/0147* (2013.01); *A61M 2025/0161* (2013.01)

(58) Field of Classification Search
CPC ...... A61M 2025/0161; A61M 25/0133; A61M 25/0136; A61M 25/0138; A61M 25/0147
See application file for complete search history.

(56) References Cited

U.S. PATENT DOCUMENTS

| 6,663,588 B2 * | 12/2003 | DuBois ............ A61M 25/0147 604/95.01 |
| 2002/0065485 A1 | 5/2002 | DuBois et al. |
| 2004/0059288 A1 * | 3/2004 | Webler ............ A61M 25/0147 604/95.04 |

OTHER PUBLICATIONS

European Search Report and Notes for the European Search Report on European Patent Application No. 14 183 053, dated Mar. 23, 2015 (7 pages).

* cited by examiner

*Primary Examiner* — Brandy S Lee

(74) *Attorney, Agent, or Firm* — Buchanan Ingersoll & Rooney PC

(57) ABSTRACT

A catheterization device including a catheter, which has a deflectable steering end, and a control device for controlling the steering end. In order to limit operating forces of the catheterization device, the control device has an energy store, which is coupled in a force-transmitting manner to a force transmission element of the control device.

15 Claims, 4 Drawing Sheets

CATHETERIZATION DEVICE COMPRISING A CATHETER, WHICH HAS A DEFLECTABLE STEERING END, AND A CONTROL DEVICE FOR CONTROLLING THE CATHETER

CROSS-REFERENCE TO RELATED APPLICATIONS

This patent application claims the benefit of U.S. Provisional Patent Application No. 61/881,977, filed on Sep. 25, 2013, which is hereby incorporated by reference in its entirety.

TECHNICAL FIELD

The present invention relates to a catheterization device comprising a catheter, which has a deflectable steering end, and a control device for controlling the steering end, wherein the control device is formed with a control arrangement that is rotatably mounted about a pivot point and that has at least one guide element arranged at a distance from the pivot point and connected in a movement-transmitting manner to the steering end.

BACKGROUND

Catheterization devices of the type mentioned in the introduction are known in general and are used for the examination and treatment of patients, for example, suffering from heart conditions. In order to guide the catheter to the heart, for example, and to examine and/or treat there a selected region of the heart, a distal end of the catheter is formed as the steering end. The steering end can be controlled and, in particular, pivoted into at least one, two, or more than two different directions by a proximal end of the catheter arranged opposite the distal end along the catheter. To pivot the steering end, a steering wire, for example, is guided from the steering end to the proximal end, where it is fixed to the control arrangement. If the control arrangement is moved about the pivot point, it pulls on the steering wire and a force attempting to deflect the steering end is conveyed to the steering end via the steering wire.

With the known catheterization devices, there is often the problem, however, that the further the steering end is to be pivoted from a rest position, the higher are the operating forces required for this purpose.

The present invention is directed toward overcoming one or more of the above-mentioned problems.

SUMMARY

Since the operating forces are generally introduced into the control arrangement manually by an operator, and high operating forces can be applied by the operator of the catheterization device only for a limited time, an object of the present invention is to provide a catheterization device that can be operated easily and in particular with a low application of force.

At least this object is achieved for the catheterization device mentioned in the introduction by an energy store which produces an auxiliary force assisting rotation of the control arrangement, wherein the control arrangement has a force transmission element that is arranged at a distance from the pivot point and the guide element, and that is coupled in a force-transmitting manner to the energy store.

Due to the energy store and the auxiliary force provided by the energy store, the force necessary for deflection, and to be introduced manually into the control arrangement, is reduced, such that the burden on the operator of the catheterization device decreases and the catheterization device can be operated more easily.

A solution according to the present invention can be further improved by different embodiments that are each advantageous alone and can be combined with one another arbitrarily. These embodiments and the advantages associated therewith will be discussed hereinafter, wherein the design measures and the effects thereof are described merely by way of example for a catheter comprising just one steering wire. Of course, the catheter may have more, and in particular two, steering wires, and the steering end thereof can thus be deflected in more than one direction by the control device.

In a first advantageous embodiment, a radius interconnecting the pivot point and the force transmission element can be oriented perpendicular to an effective-force vector of the auxiliary force, wherein an effective length of the effective-force vector is dependent on the deflection of the control arrangement from a rest position. The force transmission element is preferably rigidly connected to the guide element and, upon operation of the control device, moves together with the guide element about the pivot point. The auxiliary force may thus differ in a predefined manner or be adjusted beforehand according to the extent of the deflection of the catheter. A manual adjustment of the auxiliary force or of the effective length of the effective-force vector during the catheterization process is therefore not necessary.

In order to prevent the control arrangement from moving automatically from its rest position, the effective length in the rest position may be minimal. In particular, if the effective length is zero, the auxiliary force does not attempt to move the control arrangement from the rest position and, therefore, the rest position of the control arrangement is at least unstable or is even stable.

The effective length increases with deflection of the control arrangement from the rest position, preferably proportionally thereto. In particular with relatively small deflections, the rise is proportional. Since the effective length of the effective-force vector is dependent on the extent of the deflection of the control arrangement from its rest position, the auxiliary force may increase with the deflection of the control arrangement, such that the operating force to be introduced manually into the control arrangement is substantially constant for all possible deflections of the steering end or only changes slightly. On the whole, the forces acting on the force transmission element can substantially balance out, such that the end of the catheter remains in an arbitrary deflected position, even if the operator of the catheterization device is not holding the operating element in position.

The effective-force vector, for example, is a component of the force introduced into the force transmission element from the energy store, wherein the force introduced into the force transmission element is preferably directed to the pivot point in the rest position of the control arrangement. Since the effective length of the effective-force vector in this case is automatically zero, the auxiliary force in the rest position is likewise zero, and no measures limiting or compensating the auxiliary force in the rest position are necessary to hold the control arrangement in the rest position.

The control device may have a holding arrangement for the energy store, with the energy store being held non-displaceably on the holding arrangement, at least in the direction of the pivot point. The holding arrangement may thus be provided in a stationary manner in the control device and may hold in a stationary manner a holding end of the energy store, said holding end being arranged opposite the transmission end, which is connected to the force transmission element, of the energy store. Alternatively, the holding end supported on the holding arrangement can be held so as to be movable substantially perpendicularly by the force introduced into the force transmission element. With a movably held holding end, the effective-force length may be maximal with a deflection of the control arrangement through 90° about the pivot point and may therefore assist the operator in an optimal manner.

The force directed by the energy store in the rest position onto the force transmission element may be a tensile force. Here, the force transmission element is preferably arranged, in the rest position, behind the pivot point as considered from the holding arrangement. The control device can be constructed in a simple and compact manner as a result.

In order to design the control device so as to be even simpler and more compact, the force directed by the energy store in the rest position onto the force transmission element may be a compressive force. In this case, the force transmission element in the rest position is preferably arranged between the pivot point and the holding arrangement. The energy store producing the compressive force may thus be designed so as to be smaller and more compact than the energy store generating the tensile force.

The energy store may be a pneumatic energy store, for example, which provides the tensile force or the compressive force. The energy store preferably provides an elastic and, in particular, a spring-elastic force to assist the operation of the control device. A particularly simple and, here, very reliable energy store is a tension spring or a compression spring, for example, a coil spring, which additionally also results in low costs.

In accordance with a further advantageous embodiment, the control device may have, for example, a rand-and-pinion-like operating element, of which the teeth act on the control arrangement in a movement-transmitting manner. The control arrangement, for movement-transmitting connection to the rack, may have on its periphery at least one tooth, which engages in a form-fitting manner in at least two teeth of the rack. For example, the control arrangement can be formed as a gearwheel. A displacement of the rack-and-pinion-like operating element rotates the control arrangement. A control device of this type is compact since an operating lever protruding from a housing of the control device is not necessary, for example.

The catheterization device may have a gearing, which connects the energy store to the force transmission element in a force-transmitting manner. The strength of the force received by the force transmission element can be adapted by the gearing, or can be adapted specifically to the current requirements. In particular with relatively large deflections, it may be that the auxiliary force no longer rises proportionally with the force required for the deflection of the steering end. To adapt the auxiliary force, the catheterization device may have a gearing transmitting the auxiliary force. The gearing can be designed in such a way that the maximum possible deflection of the steering end is reached, even if the operating element has not fully reached its maximum possible deflection. The required deflection of the operating element may thus be lower. On the whole, the forces acting on the force transmission element can substantially balance out, such that the end of the catheter remains in an arbitrary deflected position, even if the operator of the catheterization device is not holding the operating element in position. The gearing is preferably designed such that the maximum possible deflection of the steering end is reached before the operating element has fully reached its maximum possible deflection. It is thus ensured that the force required to deflect the steering end changes approximately linearly with the degree of deflection, even with a large deflection of the operating element, in particular, up to the maximum possible deflection.

The catheterization device and, in particular, the catheter, may have the at least one steering wire, with which a force deflecting the steering end is transmitted from the control arrangement to the steering end. The steering wire is preferably guided on a peripheral surface of the control arrangement.

A length of a load arm, which is pivotable about the pivot point, of the control arrangement may be dependent on the deflection of the control arrangement. The load arm may extend, for example, between the pivot point and a peripheral surface of the control arrangement and, in particular, the disk-shaped base. The steering wire may bear against the peripheral surface. The peripheral surface may have different distances from the pivot point, said distances, for example, being continuous in their course, whereby the force to deflect the steering end can be adapted to the degree of deflection. The catheterization device can be produced more easily, however, if the length of the load arm is independent of the deflection of the control arrangement from the rest position. To this end, the peripheral surface preferably has a constant distance from the pivot point. For example, a disk-shaped base of the control arrangement can be formed in a circular manner, at least in part and, in particular, in guide portions against which the steering wire bears according to the deflection of the control arrangement.

The auxiliary force is preferably strong enough to hold the steering end in a deflected position. In particular, if no external forces act on the steering end, the auxiliary force, where possible together with frictional forces acting within the catheterization device, may prevent an undesirable pivoting of the steering end from the set pivot position. If external forces occur that act on the steering end and attempt to deflect it, the auxiliary force, again where possible together with frictional forces acting within the catheterization device, can be set or can be adjustable such that the steering end retains the set pivot position in spite of the external forces.

The control device described and presented in the exemplary embodiments described herein can also be provided without the catheter(s) or as a set comprising a plurality of catheters, of which at least some are not connected in a movement-transmitting manner to the control arrangement.

The present invention is explained hereinafter by way of example on the basis of exemplary embodiments with reference to the drawings. The different features of the embodiments can be combined herein independently of one another, as has already been explained with the individual advantageous embodiments.

Further features, aspects, objects, advantages, and possible applications of the present invention will become apparent from a study of the exemplary embodiments and examples described below, in combination with the Figures, and the appended claims.

DETAILED DESCRIPTION

Figure 1:
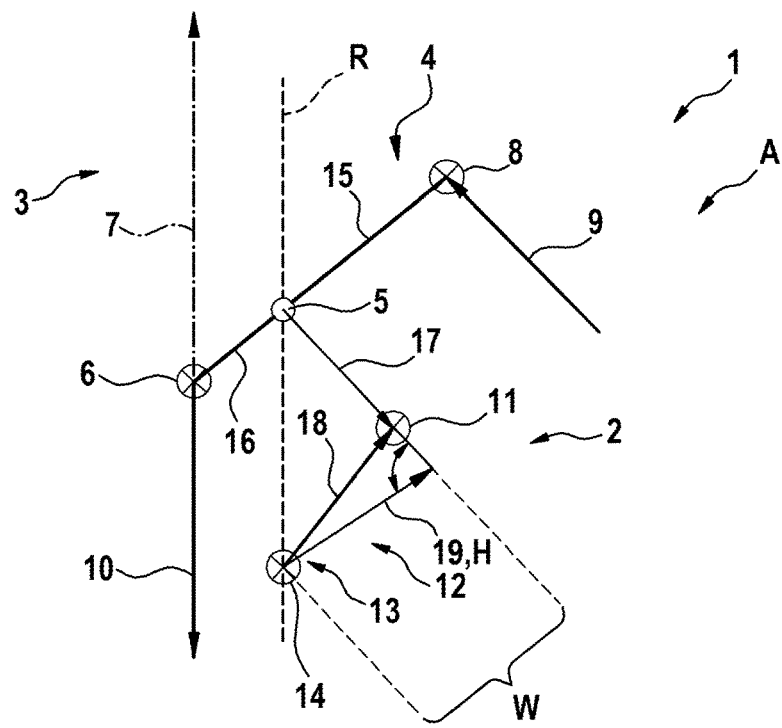
FIGS. 1-4 show different schematic exemplary embodiments of the catheterization device according to the present invention.

FIG. 1 shows a schematic view of the catheterization device 1 with a control device 2 and a catheter 3.

The control device 1 is illustrated with a control arrangement 4. The control arrangement 4 is shown in FIG. 1 in a highly schematic manner and merely with levers, force transfer or force delivery elements, and a pivot point 5. The control arrangement 4 is mounted in the control device 2 rotatably about the pivot point 5 running perpendicular to the drawing plane. The pivot point 5 converts forces acting on the control arrangement 4 into torques and, in particular, passes operating forces on to the steering end of the catheter 3.

The control arrangement 4 has a guide element 6, which can be connected in a movement-transmitting manner to the steering end. In the exemplary embodiment of FIG. 1, the guide element 6 is connected in a movement-transmitting manner to a steering wire 7 of the catheter 3. The steering wire 7 can be fixed to the guide element 6 and, for example, can be fixed in place by a screw connection. Furthermore, the control arrangement 4 has an operating element 8, into which an operator of the catheterization device can introduce an operating force 9 to deflect the steering end. The control arrangement 4 and the pivot point 5 convert the operating force 9 into a deflection force 10 which, for example, is formed as a tensile force and attempts to deflect the steering wire in order to deflect the steering end from a rest position.

The control device 2 is further formed with a force transmission element 11, which is formed at a distance from the pivot point 5 and the guide element 6 by the control arrangement 4. The guide element 6, the operating element 8 and the force transmission 11 are preferably interconnected in a movement-transmitting manner and, more preferably, rigidly.

In addition, the control device 2 is shown with an energy store 12, of which the holding end 13 is fastened to a holding arrangement 14. The holding arrangement 14 is preferably received in the control device 2 non-displaceably at least in the direction of the pivot point 5.

A rest position R of the control device 2 is indicated by a dashed line cutting the pivot point 5. If an operating position of the control arrangement 4 corresponds to the rest position R, the control arrangement 4 is thus located in its rest position, and the steering end of the catheter 3 is therefore not deflected. For example, a force arm 15 of the control arrangement 4, with said force arm connecting the pivot point 5 with the operating element 8, is oriented perpendicular to the dashed line in the rest position R. A load arm 16, which extends from the pivot point 5 to the guide element 6, may also run perpendicular to the dashed line in the rest position R. A radius 17 running from the pivot point 5 to the force transmission element 11 is oriented parallel to the dashed line in the rest position R. In particular, the radius 17 in the rest position R points from the pivot point 5 to the holding arrangement 14.

In FIG. 1, the control arrangement 4 is not illustrated in its rest position, but in a deflection position A, and the control arrangement 4 is deflected from is rest position in an anti-clockwise direction by the operating force 9 introduced into the operating element 8. The steering wire 7 is displaced in the direction of the deflection force 10 compared to the rest position. The force transmission element 11 arranged in the rest position between the pivot point 5 and the holding arrangement 14 is likewise deflected in an anti-clockwise direction.

A force of the energy store 12 acts mechanically on the force transmission element 11, wherein the force delivered by the energy store 12 is illustrated as a force vector 18, which points from the holding arrangement 14 to the force transmission element 11. The energy store 12 thus stores a compressive force, which acts on the force transmission element 11 and attempts to push it further from the rest position in an anti-clockwise direction.

The compressive force of the energy store 12, illustrated by the force vector 18, does not fully push the force transmission element 11 further from the rest position, however. Merely a component of the force vector 18 and, in particular, a component of the effective-force vector 18, illustrated as an effective-force vector 19 and running perpendicular to the radius 17, attempts to further deflect the force transmission element 11. An effective length W, determined by the magnitude of the effective-force vector 19, changes according to the operating position of the control arrangement 4. If the control arrangement 4 is oriented in the rest position, the effective length W is thus minimal and, in particular, zero, since the force vector 18 points from the holding arrangement 14 to the pivot point 5. Since the radius 17 and the force vector 18 are oriented in opposite directions in the rest position of the control arrangement 4, the effective-force vector 19, running perpendicular to the radius 17, of the force vector 18 is equal to zero. The force introduced by the energy store 12 into the force transmission element 11 therefore, in the rest position of the control arrangement 4, does not cause the control arrangement 4 to be moved from the rest position R.

If the control arrangement 4 is moved out of its rest position and, for example, turns about the pivot point 5 in an anti-clockwise direction, the effective length W of the effective-force vector 19 thus rises proportionally to the deflection of the control arrangement 4 from the rest position. The effective length W of the effective-force vector 19 is proportional to an auxiliary force H, which assists the operator when operating the steering end.

Figure 2:
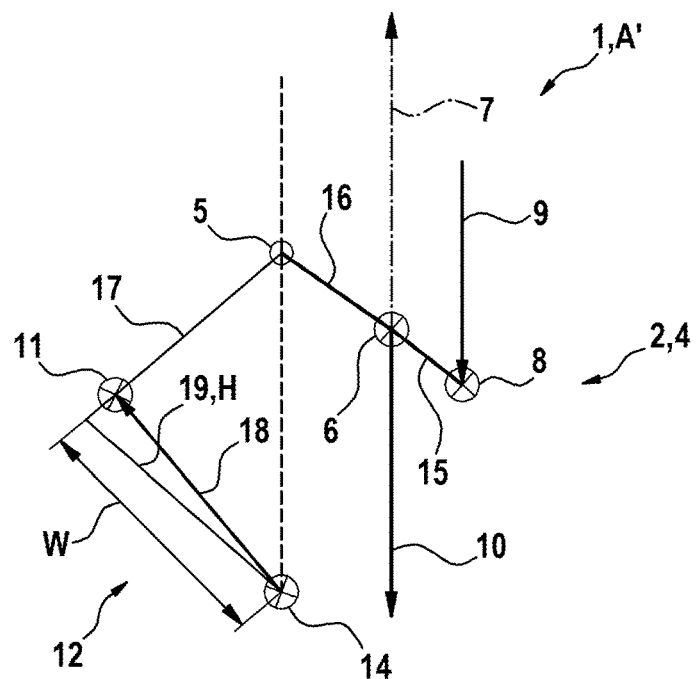

FIG. 2 shows a further exemplary embodiment of the present invention, wherein the same reference signs have been used for elements that correspond in terms of function and/or structure to the elements in the exemplary embodiment in FIG. 1. For the sake of brevity, and as will be understood by one skilled in the art, merely the differences from the exemplary embodiment of FIG. 1 will be discussed.

The catheterization device 1 is likewise illustrated in a deflection position A' in the exemplary embodiment of FIG. 2, and has all elements of the catheterization device 1 of the exemplary embodiment 1. In contrast thereto, the force arm 15 and the load arm 16 are not arranged pointing away from one another on different sides on the pivot point 5, however. As shown in the exemplary embodiment of FIG. 2, the force arm 15 and the load arm 16 can be arranged on the same side of the pivot point 5 and, in particular, overlapping one another in order to enable a more compact structure of the control device 2.

Figure 3:
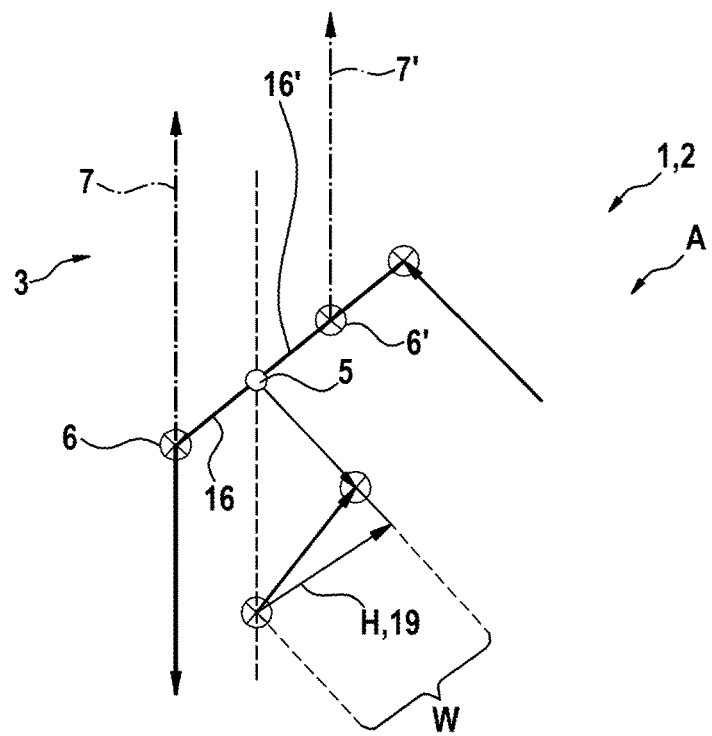

FIG. 3 shows a further exemplary embodiment of the present invention, wherein the same reference signs are used for elements that correspond in terms of function and/or structure to the elements in the exemplary embodiments in FIGS. 1-2. For the sake of brevity, and as will be understood by one skilled in the art, merely the differences from the exemplary embodiments in the previous Figures will be discussed.

The catheter 3 of the exemplary embodiment in FIG. 3 has a steering end that can be deflected in different directions. In particular, the steering end of the catheter 3 is pivotable in directions pointing away from one another. In order to be able to pivot the steering end of the catheter 3 in both directions, the catheter 3 is equipped with two steering wires 7, 7'. The steering wire 7 is fastened to the guide element 6, as in the exemplary embodiment in FIG. 1. The guide element 6 is connected via the load arm 16 to the pivot point 5. The steering wire 7' is attached to a further guide element 6', wherein the guide element 6' is connected by a further load arm 16' to the pivot point 5. In order to be able to pivot the steering end in opposite directions, the load arms 16, 16' point away from the pivot point 5 in different and, in particular, opposite directions. The pivot point 5 is thus preferably arranged between the guide elements 6, 6'.

Figure 4:
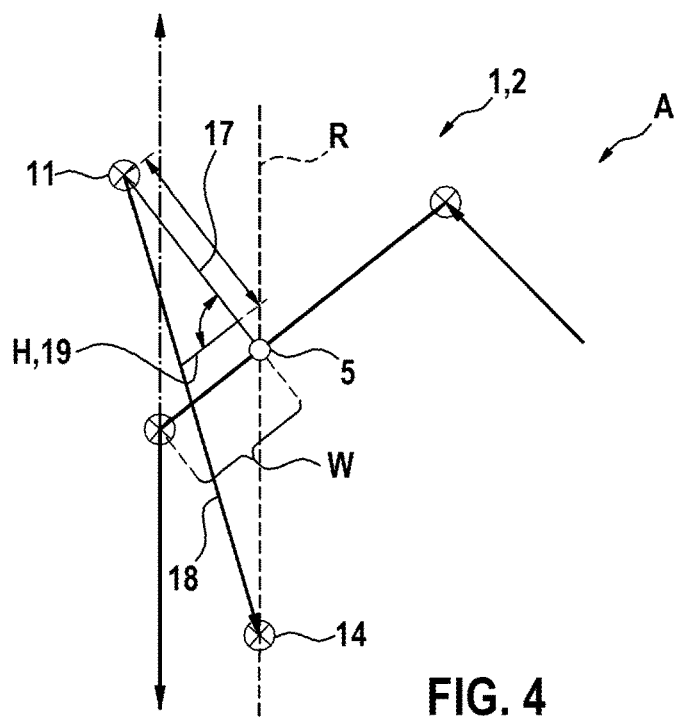

FIG. 4 shows a further exemplary embodiment of the present invention, wherein the same reference signs are used for elements that correspond in terms of function and/or structure to the elements in the exemplary embodiments in the previous Figures. For the sake of brevity, and as will be understood by one skilled in the art, merely the differences from the previous exemplary embodiments will be discussed hereinafter.

The catheterization device 1 is illustrated in FIG. 4 with a control device 2, of which the force transmission element 11 is arranged behind the pivot point 5 as considered from the holding arrangement 14. In the rest position R of the control arrangement 4, the pivot point 5 can be arranged between the force transmission element 11 and the holding arrangement 14.

The force vector 18 of the force acting on the force transmission element 14 and produced by the energy store 12 points from the force transmission element 11 in the direction of the holding arrangement 14. The force generated by the energy store 12 is thus a tensile force.

Figure 5:
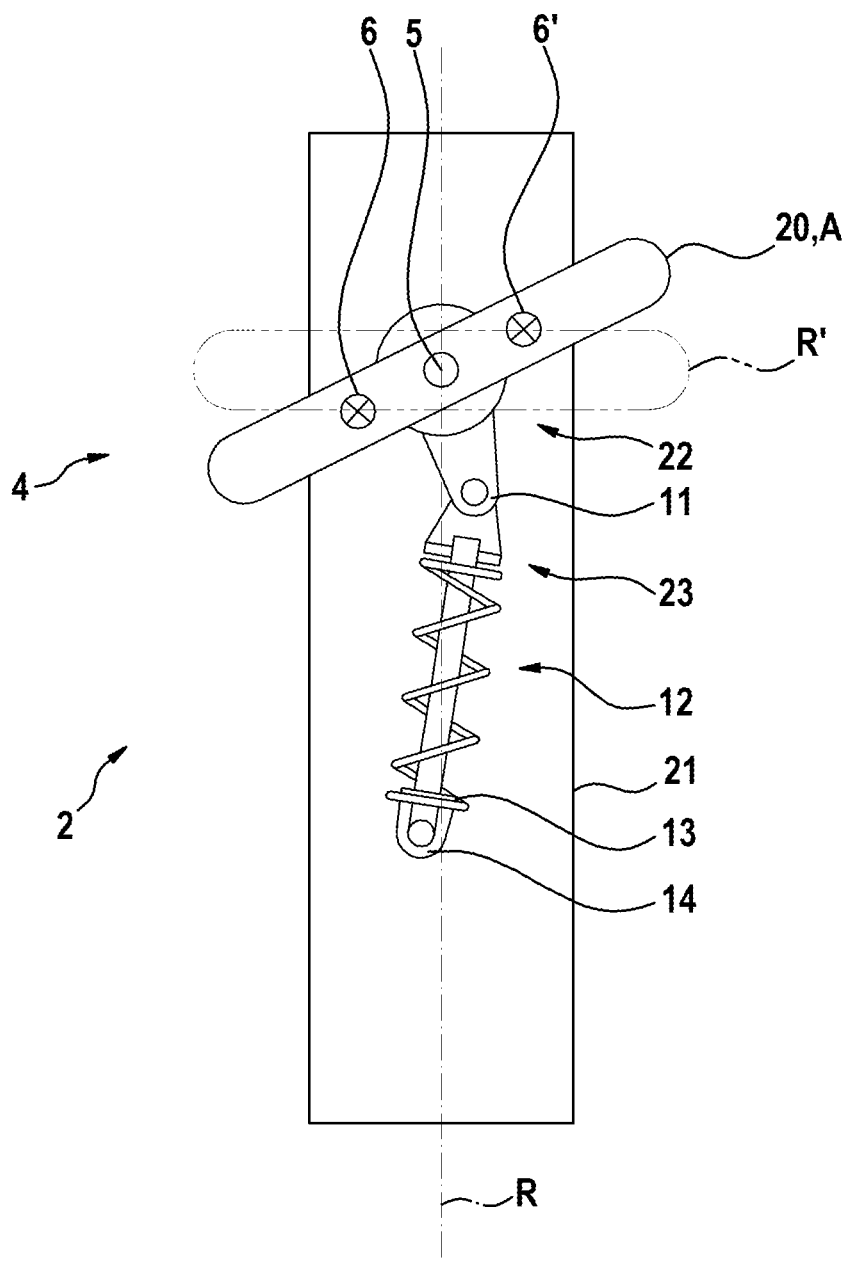
FIG. 5 shows a schematic view from above of a further exemplary embodiment of the catheterization device according to the present invention

FIG. 5 shows a schematic view from above of an exemplary embodiment of the control device 2 of the exemplary embodiment in FIG. 3. The same reference signs are used for elements that correspond in terms of function and/or structure to the elements in the exemplary embodiment in FIG. 3. For the sake of brevity, and as will be understood by one skilled in the art, merely the differences from the exemplary embodiment in FIG. 3 will be discussed hereinafter.

The control arrangement 4 is formed with an operating lever 20, which is held rotatably in a housing 21 via the pivot point 5. The housing 21 is illustrated transparently at least in part so as to be able to illustrate details of the exemplary embodiment in FIG. 5.

The force transmission element 11 is formed as a lever, extending away from the pivot point 5, of an eccentric 22 rotatable about the pivot point 5. The eccentric 22 is connected in a movement-transmitting manner to the operating lever 20 and is screwed or otherwise connected thereto, for example. The holding end 13 of the energy store 12 is mounted non-displaceably in the housing 21 by the holding arrangement 14, but pivotably about a pivot point extending parallel to the pivot point 5. A transmission end 23 of the energy store 12 arranged opposite the holding end 13 is fixed in a movement-transmitting manner to the force transmission element 11, wherein the transmission end 23 is pivotable relative to the force transmission element 11 about a further pivot point extending parallel to the pivot point 5.

The control arrangement 4 is shown in the deflection position A. The rest position R' of the control arrangement 4 is shown by the dashed illustration of the operating lever 20, wherein the operating lever 20 extends perpendicular to the dashed line R in the rest position R'. The force transmission element 12, in the rest position R', runs from the holding arrangement 14 in the direction of the pivot point 5 along the dashed line R.

Figure 6:
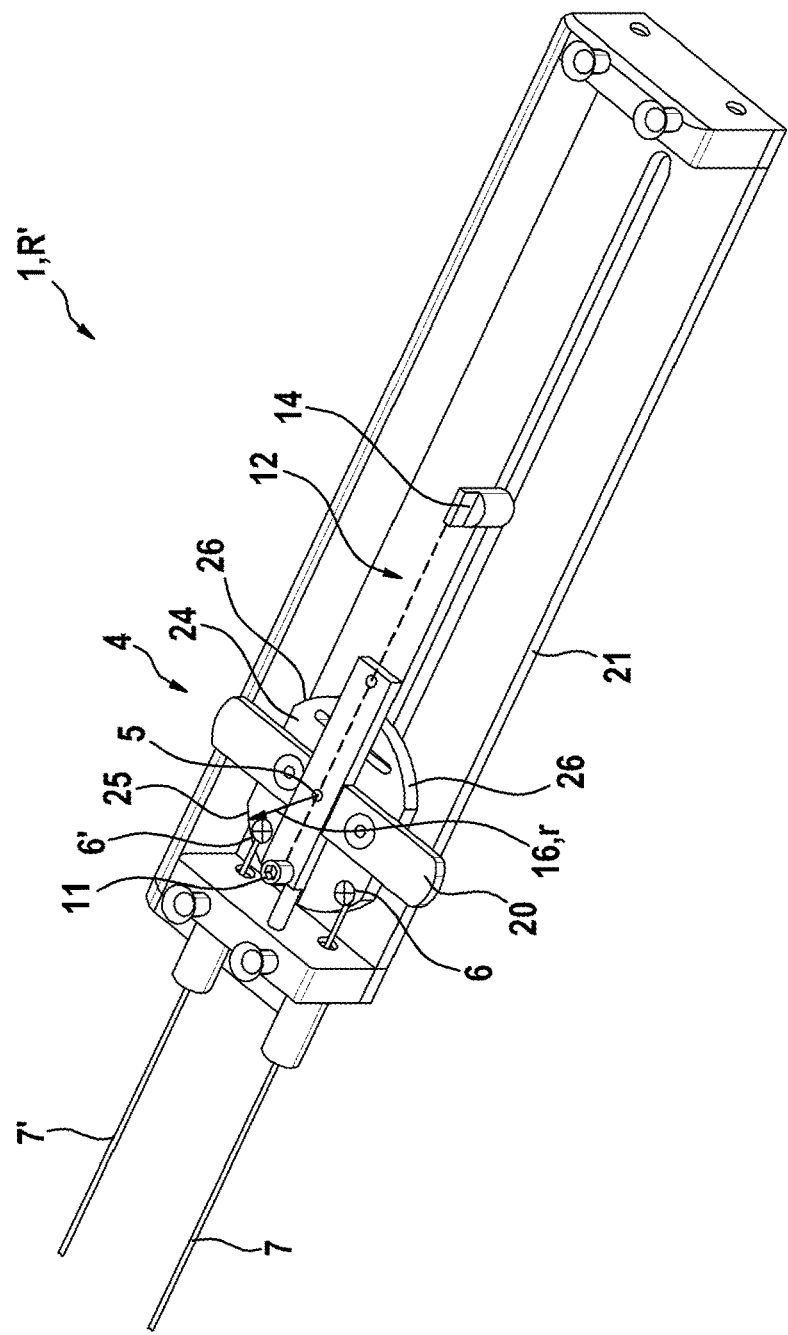
FIG. 6 shows a schematic perspective view of a further exemplary embodiment of the catheterization device according to the present invention.

FIG. 6 shows a schematic perspective view of a further exemplary embodiment of the catheterization device 1. The same reference signs are used for elements that correspond in terms of function and/or structure to the elements in the previous exemplary embodiments. For the sake of brevity, and as will be understood by one skilled in the art, merely the differences from the previous exemplary embodiments will be discussed.

The control arrangement 4 is illustrated in the exemplary embodiment in FIG. 6 in the rest position R'. The catheterization device 1 shown in FIG. 6 is also formed with the operating lever 20, which is formed about the pivot point 5 in the housing 21. The housing 21 is again illustrated transparently in part so as to be able to better illustrate details of the catheterization device 1.

The force vector 18 of the force provided by the energy store 12 points toward the holding arrangement 14 and constitutes a tensile force, which draws the force transmission element 11 in the direction of the holding arrangement 14. The force transmission element 11 is arranged behind the pivot point 5, as considered from the holding arrangement 14, and additionally behind the operating lever 20.

The force transmission element 11 is fastened to a disk-shaped base 24, which interconnects the force transmission element 11, the operating lever 20, and also the steering wires 7, 7' in a movement-transmitting manner. The disk-shaped base 24 is preferably received and mounted in the catheterization arrangement 1 non-displaceably, but rotatably about a pivot point. To fasten the steering wires 7, 7', the guide elements 6, 6' are provided on the base 23 behind the operating lever 20, as viewed from the holding arrangement 14 and in front of the force transmission element 11, wherein the guide elements 6, 6' are preferably arranged between the pivot point 5 and the force transmission element 11.

The steering wires 7, 7' may each be fastened to the holding arrangement 14 and, in particular, to the disk-shaped base 24 thereof such that at least one of the steering wires 7, 7', when the base 24 is deflected, sweeps over this such that the length of a component of the load arm 16 running perpendicular to the energy store 12 changes when the holding arrangement 14 is moved from the rest position R'. The component may equally be referred to as the effective length of the load arm 16.

In the exemplary embodiment in FIG. 6, the base 24 is formed, however, with at least one peripheral surface 25, against which one of the steering wires 7, 7' bears and is preferably guided when the control arrangement 4 is deflected from the rest position R'. If the peripheral surface 25 has a constant distance from the pivot point 5, which, for example, corresponds to the radius r of the peripheral surface 25 in the region of a guide portion 26 of the control arrangement 4 for guiding the steering wire 7, 7', the effective length of the load arm 16 is, for example, constant irrespective of the holding arrangement 14.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A catheterization device comprising:
a catheter including a deflectable steering end, and a control device for controlling the deflectable steering end, wherein the control device is formed with a control arrangement which is mounted rotatably about a pivot point and which has at least one guide element arranged at a distance from the pivot point and connected in a movement-transmitting manner to the deflectable steering end,
wherein the control device further includes an energy store, which produces an auxiliary force (H) assisting a rotation of the control arrangement, wherein the control arrangement has a force transmission element which is arranged at a distance from the pivot point and the guide element and which is coupled in a force-transmitting manner to the energy store, and
wherein the force transmission element is connected to a disk-shaped base rotatable about the pivot point, wherein rotation of the disk-shaped base interconnects the force transmission element, the control arrangement and the at least one guide element in a movement-transmitting manner.

2. The catheterization device as claimed in claim 1, wherein a radius interconnecting the pivot point and the force transmission element is oriented perpendicular to an effective-force vector of the auxiliary force (H), wherein an effective length (W) of the effective-force vector is dependent on a deflection of the control arrangement from a rest position.

3. The catheterization device as claimed in claim 2, wherein the effective length (W) in the rest position is minimal.

4. The catheterization device as claimed in claim 2, wherein the effective length (W) rises with the deflection of the control arrangement from the rest position.

5. The catheterization device as claimed in claim 2, wherein the effective-force vector is a component of the force introduced into the force transmission element from the energy store, wherein the force introduced into the force transmission element is directed toward the pivot point in the rest position of the control arrangement.

6. The catheterization device as claimed in claim 2, wherein the force directed onto the force transmission element by the energy store in the rest position is a tensile force, and wherein the force transmission element is arranged between the pivot point and the holding arrangement in the rest position.

7. The catheterization device as claimed in claim 6, wherein the energy store is a tension spring.

8. The catheterization device as claimed in claim 2, wherein the force directed onto the force transmission element by the energy store in the rest position is a compressive force, and wherein the force transmission element, in the rest position, is arranged between the pivot point and the holding arrangement.

9. The catheterization device as claimed in claim 8, wherein the energy store is a compression spring.

10. The catheterization device as claimed in claim 2, wherein a length of a load arm, pivotable about the pivot point, of the control arrangement is independent of the deflection of the control arrangement from the rest position.

11. The catheterization device as claimed in claim 1, wherein the control device includes a holding arrangement in the energy store, with the energy store being held non-displaceably on the holding arrangement, at least in the direction of the pivot point.

12. The catheterization device as claimed in claim 1, further comprising a gearing which connects the energy store to the force transmission element in a force-transmitting manner.

13. The catheterization device as claimed in claim 1, further comprising at least one steering wire which is guided on a peripheral surface of the control arrangement.

14. The catheterization device as claimed in claim 1, wherein the auxiliary force is strong enough to hold the deflectable steering end in a deflected position.

15. The catheterization device as claimed in claim 1, wherein the control arrangement comprises an operating lever, and wherein the at least one guide element comprises two guide elements connected to the operating lever on opposite sides of the pivot point.

* * * * *